United States Patent [19]

Mastronardi et al.

[11] Patent Number: 5,531,713
[45] Date of Patent: Jul. 2, 1996

[54] NEEDLE CATHETER WITH SAFETY DEVICE

[75] Inventors: Pasquale Mastronardi, Napoli; Antonio E. Rossi, Aversa; Fiorentino Fraganza, Cancello Arnone, all of Italy

[73] Assignee: Industria Prodotti Medicinali I.P.M. S.r.L., Calcio, Italy

[21] Appl. No.: 232,202

[22] PCT Filed: Oct. 28, 1992

[86] PCT No.: PCT/EP92/02458

§ 371 Date: Apr. 29, 1994

§ 102(e) Date: Apr. 29, 1994

[87] PCT Pub. No.: WO93/08865

PCT Pub. Date: May 13, 1993

[30] Foreign Application Priority Data

Oct. 31, 1991 [IT] Italy .................. MI91A2897

[51] Int. Cl.⁶ .................................................. A61M 5/00
[52] U.S. Cl. ........................ 604/263; 604/51; 604/158; 604/162; 604/164; 604/171
[58] Field of Search ........................... 604/263, 51, 52, 604/53, 93, 110, 117, 158, 159, 161, 162, 164, 171, 239, 244, 245, 264, 272, 192, 194, 195, 196

[56] References Cited

U.S. PATENT DOCUMENTS

| 4,160,450 | 7/1979 | Doherty . | |
| 4,245,635 | 1/1981 | Kontos . | |
| 4,755,170 | 7/1988 | Golden . | |
| 4,944,728 | 7/1990 | Carrell et al. . | |
| 5,015,240 | 5/1991 | Soproni et al. | 604/192 |
| 5,051,109 | 9/1991 | Simon . | |
| 5,064,083 | 11/1991 | Alexander et al. | 215/247 |

FOREIGN PATENT DOCUMENTS

| 0194886 | 3/1986 | European Pat. Off. . |
| 0449510 | 3/1991 | European Pat. Off. . |
| 2636812 | 8/1976 | Germany . |

Primary Examiner—Corrine M. Maglione
Assistant Examiner—N. Kent Gring
Attorney, Agent, or Firm—Bucknam and Archer

[57] ABSTRACT

A needle catheter particularly for endovasal use, including a needle-guide or metallic mandrel (1) fitted with an end grip (2), and a catheter (4) with an end casing (5). Between the end grip (2) of the metallic needle (1) and the casing (5) of the catheter (4), there is an extensible element (9), (9') acting as a cover for the metallic needle (1) after its extraction. A tap, a ball or at least one vane is provided for blocking the lumen of the casing, movable from a position where it does not obstruct the lumen (11) of the catheter, to a position where it occludes the lumen.

5 Claims, 11 Drawing Sheets

NEEDLE CATHETER WITH SAFETY DEVICE

This invention relates to a needle catheter to be placed in the lumen of a blood vessel, for example for the administration of anaesthetics drugs or drips or for similar uses and equipped with a safety device, in particular against possible injury to the user or to other personnel.

A needle catheter consists of a needle-guide or metallic mandrel enclosed in a catheter made of plastic material. In practice, the whole is inserted in the blood vessel like a normal needle and then the metallic needle-guide is extracted, to allow, for example, a drip to be connected to the catheter for administration to the patient.

This type of needle catheter is superseding ordinary metallic needles because of its indisputable advantages among which are: ease of endovasal positioning, greater freedom of movement for the patient who can move his limbs without danger of damaging the blood vessel and longer lasting patency.

However, two major disadvantages must be added to these qualities and these represent a potential danger of transmission of infective pathology.

These disadvantages are connected with the extraction of the needle-guide or metallic mandrel for the connection of the catheter to a drip or other device and the consequent bleeding.

While it is possible to protect oneself from the blood flow by using gloves for example and thereby considerably reducing the risk of contagion, this is not possible, either during the extraction of the metallic needle or later on, so that it is easy to be pricked and possibly infect oneself because surgical gloves are by no means imperforable.

The object of the invention is to eliminate these disadvantages, and in particular the risk of injury to the user or other personnel with the metallic needle-guide.

This objective is achieved, by the means of the invention, in providing an extending cover element, joining the end grip of the needle-guide to the casing of the catheter, in such a way as to cover the needle when this is withdrawn from the catheter, means of blocking being provided to fix the metallic needle in the withdrawn position as well as a means of interception to prevent the outflow of blood.

This extensible cover, best takes the form of telescopic sections or of an elastic element such as a bellows.

A flexible lateral branch for joining to a drip or other item can be fixed to the catheter at a point above the means of interception.

This means of interception and possibly of blocking can take the form of an adjustable vane in appropriate guides set in the body of the catheter, in such a way as to create a barrier in the lumen of the catheter when it is lowered.

Alternatively a ball can be set in an appropriate space in the casing of the catheter and which is forced into the lumen thus occluding it.

Again, a tap can be provided, consisting of a ball valve or other equivalent means, actioned by an external lever.

The needle once extracted can remain in situ, inside the extensible element which remains attached to the catheter. It is however better to completely remove the needle-guide together with the extensible covering element.

Further features of the invention will be clarified by the detailed description which follows and which is simply an example and therefore not limitative in its application. It is illustrated by the enclosed drawings of which.

Figure 1:
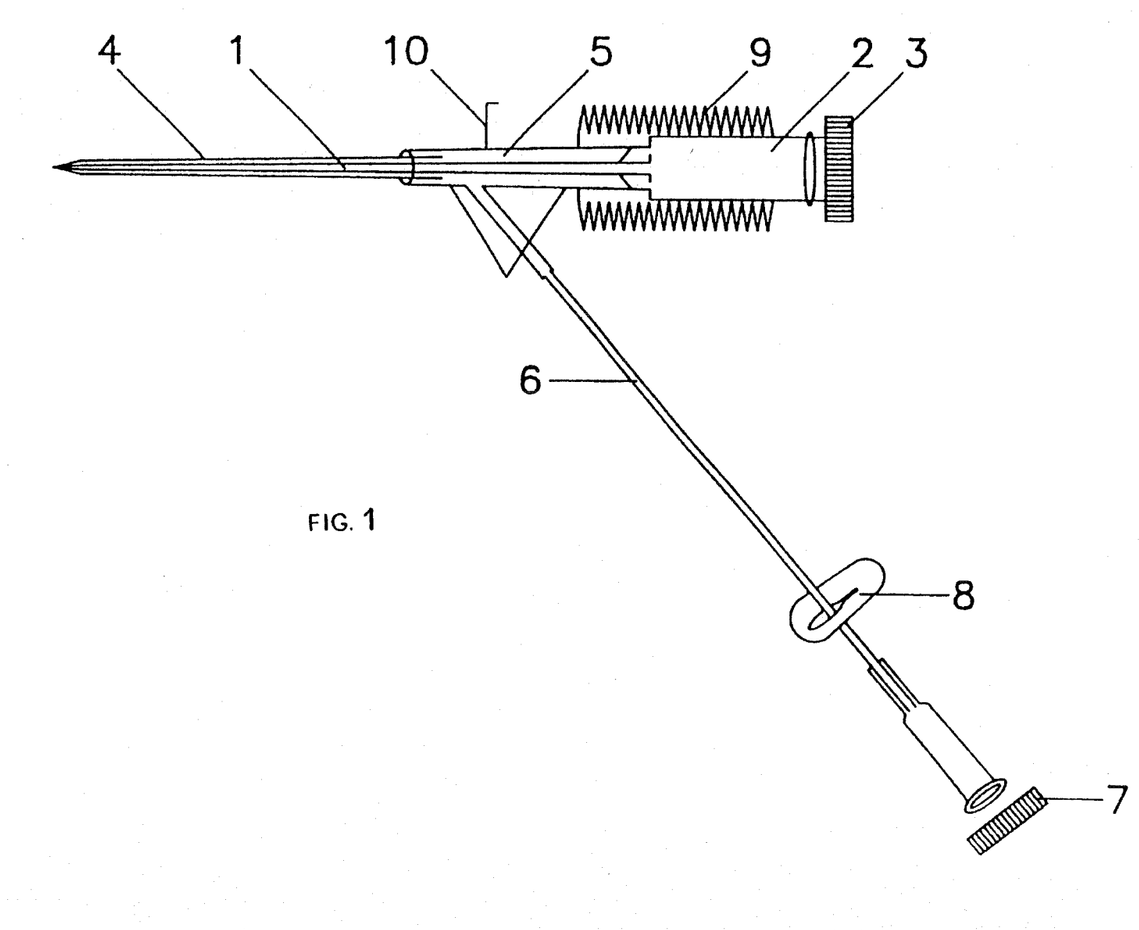
FIG. 1 represents a lateral schematic view, partly in section, of a needle catheter complete with the safety device according to the invention, in its first form of construction, before retraction of the metallic needle-guide.
Figures 2, 3A, 3B:
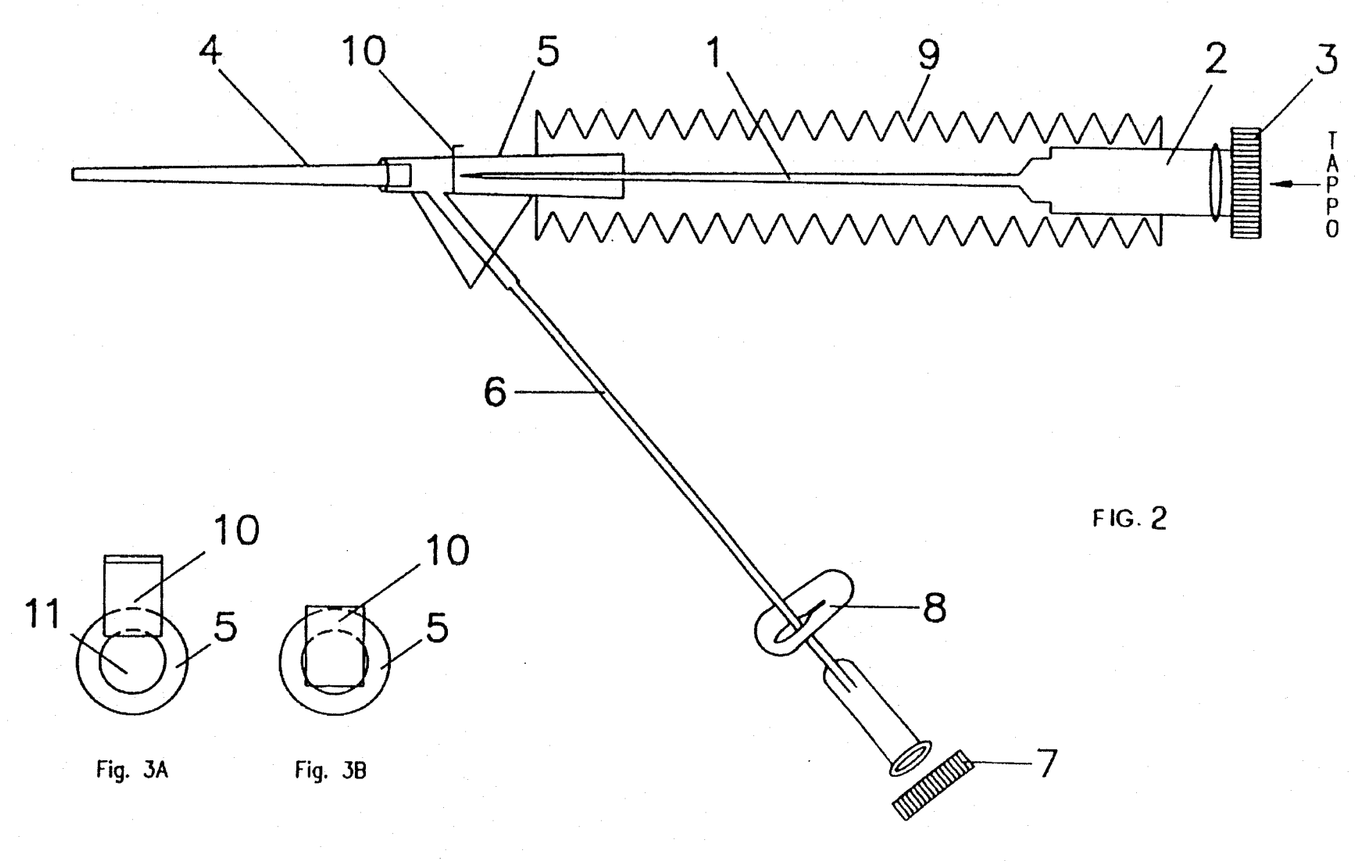
FIG. 2 is the same view as FIG. 1 but with the needle-guide retracted.
FIGS. 3A and 3B are enlarged schematic sections at the point of the adjustable vane which is shown in the open and closed positions respectively.

Referring firstly to FIGS. 1 and 2, the needle catheter according to the first construction form of the invention comprises a needle-guide or metallic mandrel (1) fitted with an end grip (2) closed by a threaded plug (3) and a catheter (4) surrounding the needle (1) and provided at the top end with a grip or casing (5) to which a flexible lateral branch may be attached (6) for the connection of a drip for example; the branch may be fitted at its extremity with a threaded plug (7) and with temporary closing of the flow (8) in an intermediate section.

Between the casing 5 of the catheter 4, and the grip (2) of the metallic needle (1) an extensible elastic element is disposed, in particular a bellows (9) which can be produced by die-casting with the other elements or be soldered at the respective ends.

An adjustable vane (10) is placed in the casing (5) of the catheter (4) above the bellows (9) and is movable from a raised position to a lowered position in which it occludes the lumen (11) (FIGS. 2 and 3B).

The functioning of the needle catheter according to the invention is as follows:

Once it has been inserted into the lumen of the blood vessel (FIG. 1) the needle guide or metallic mandrel (1) is retracted and the adjustable vane (10) (FIG. 2) is lowered, having the form of an inverted "L", and which, in addition to stopping the blood, blocks the needle-guide (1) which thus remains enclosed in the bellows (9) which is attached to the catheter casing (5). In this way, any possibility of contagion is eliminated, either during use of the needle catheter or during its dismantling.

The other forms of construction of the invention are now described, in using the same reference numbers as used in the construction according to FIGS. 1 and 2, so as to identify equal or similar parts and in adding an apostrophe to these numbers to distinguish and identify corresponding parts.

Figure 4:
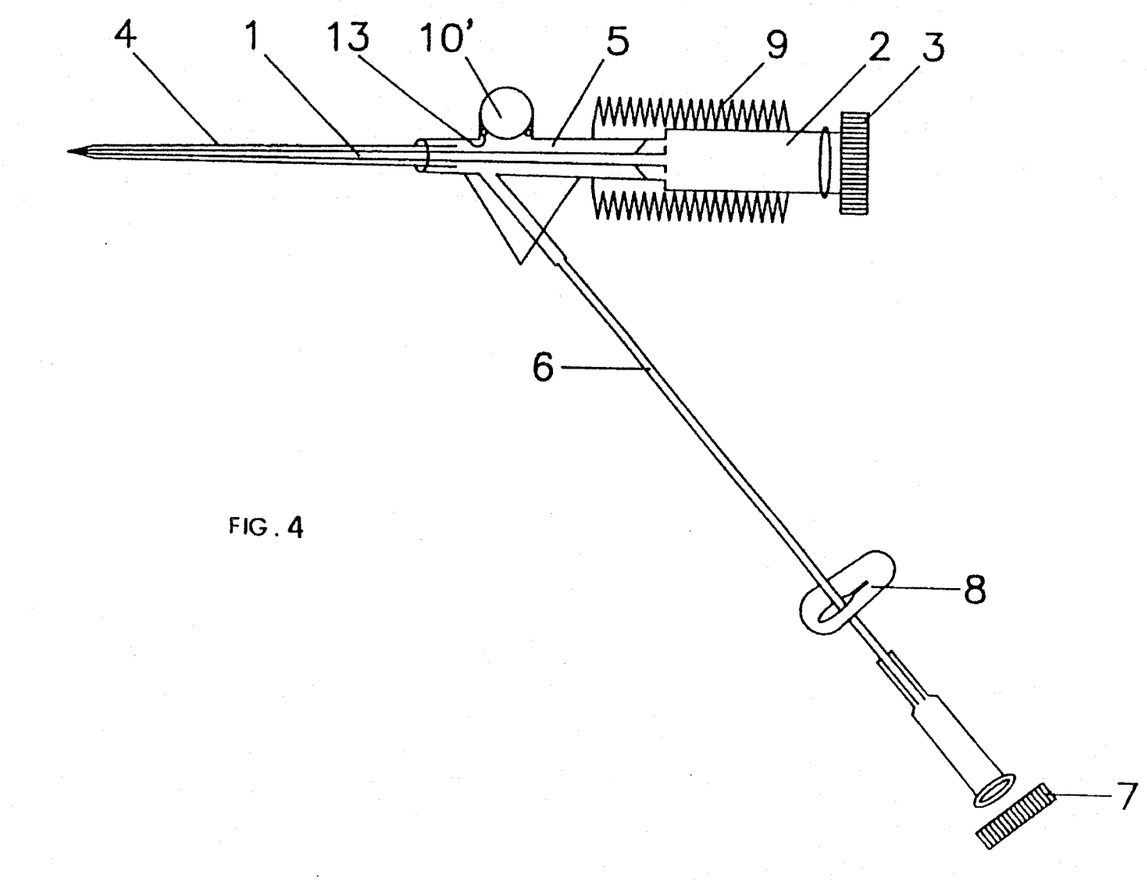
FIGS. 4 and 5 show similar views to FIGS. 1 and 2 and illustrate a second form of construction for the invention.
Figure 5:
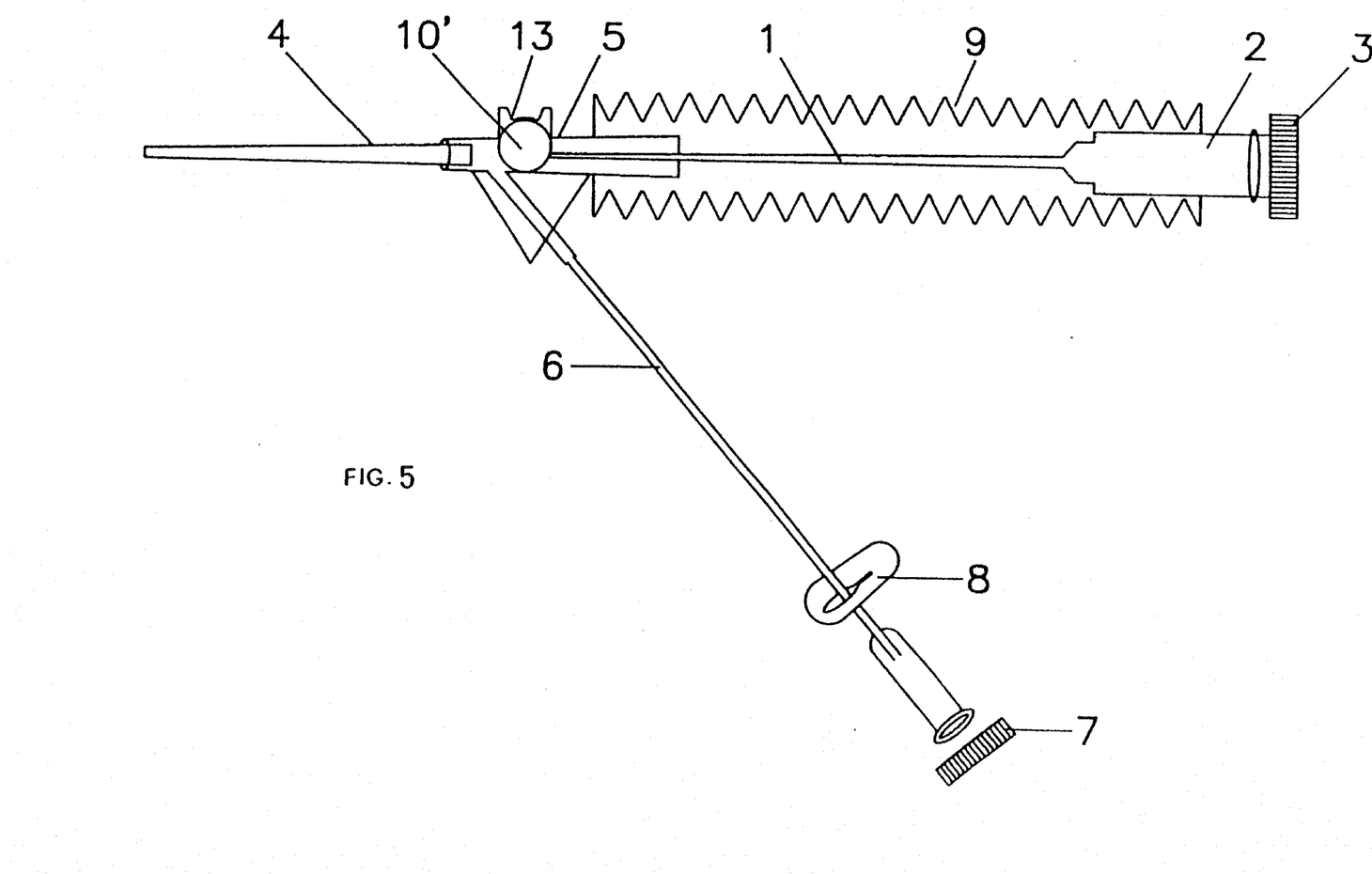

The construction illustrated in FIGS. 4 and 5 differs from that in FIGS. 1 and 2 only by the fact that the means of blocking the metallic needle (1) consists of a ball (10') contained in a pliable housing (13) (like a tablet blister) which allows the ball to escape by simple downward pressure so that it occludes the catheter lumen as shown in FIG. 5.

Figure 6:
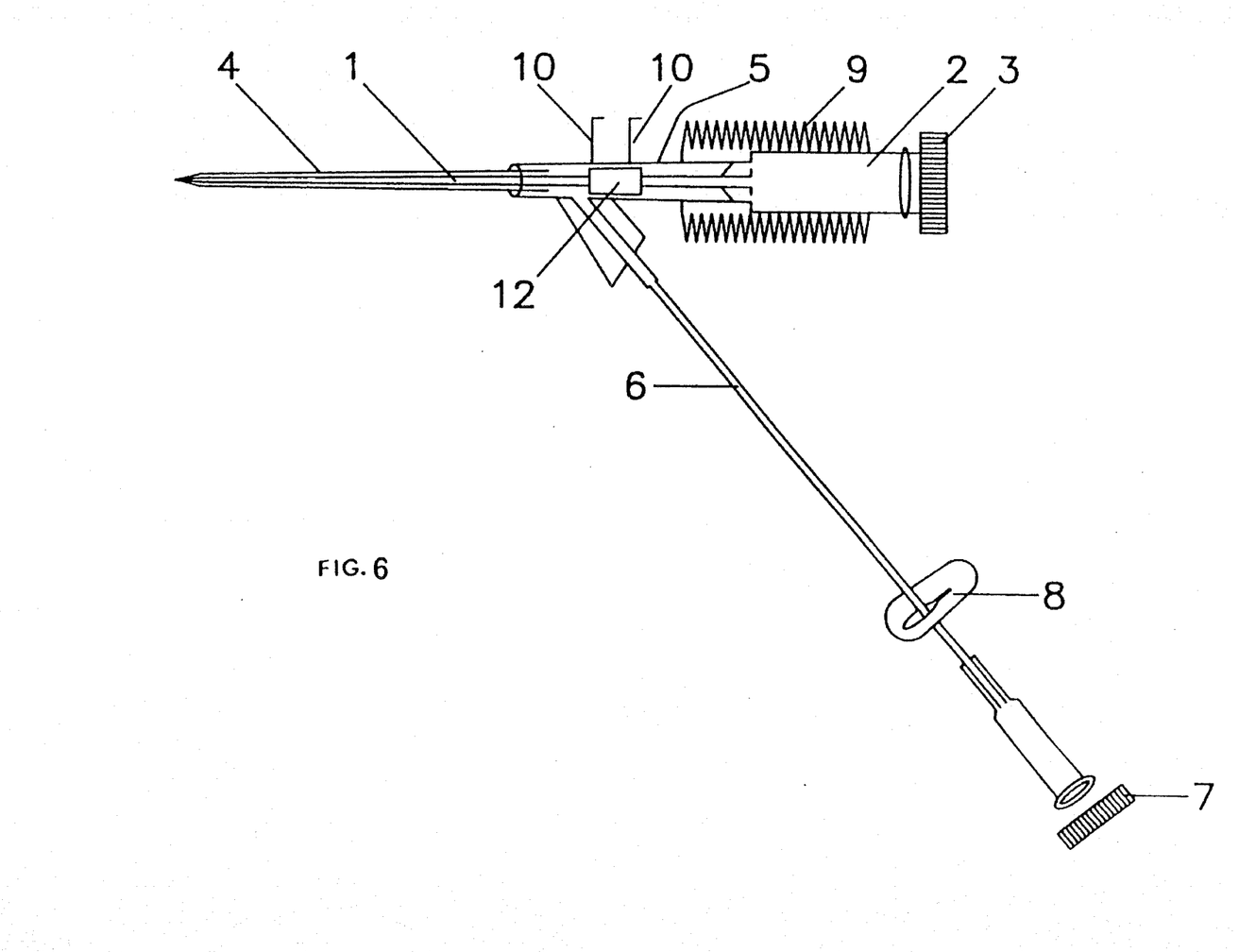
FIGS. 6 and 7 again show similar views to FIGS. 1 and 2 and illustrate a third form of construction for the invention.
Figure 7:
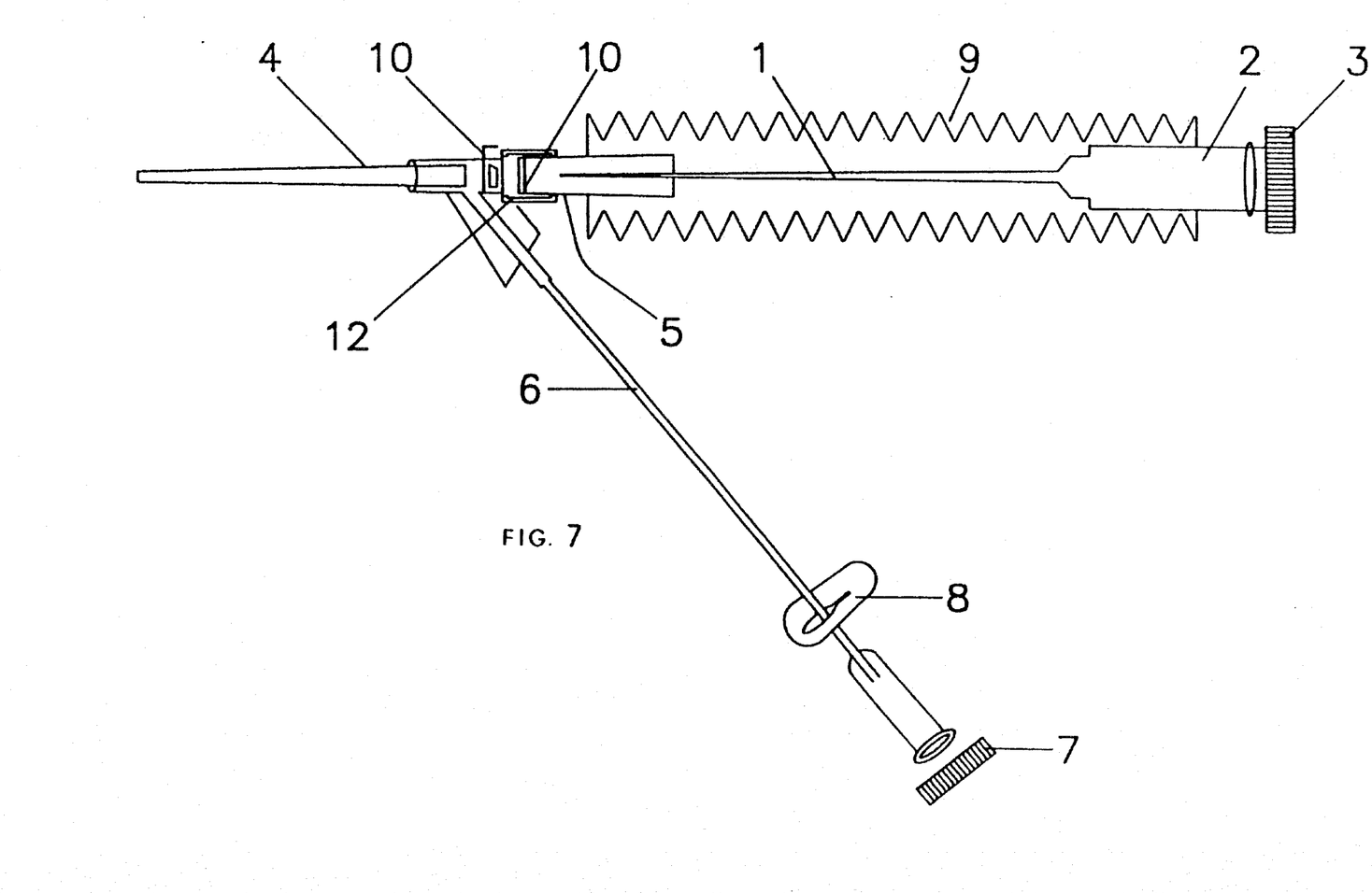

According to the construction shown in FIGS. 6 and 7, two adjustable vanes (10) are fitted in the casing (5) of the catheter (4) and the casing (5) is divided into two parts in correspondence with the zone included between the vanes and between which parts there is a screwed, grooved or similar connection, shown schematically in these Figures and indicated by the reference number (12).

Once the catheter (4) has been placed in the vasal lumen, and the needle (1) has been retracted, both of the vanes (10) are lowered and the opposed part of the casing (5) of the catheter to which the bellows (9) are attached, is released (FIG. 7). In this way, the metallic needle (1) which stays fixed in the bellows (9) can be completely removed and disposed of.

Figure 8:
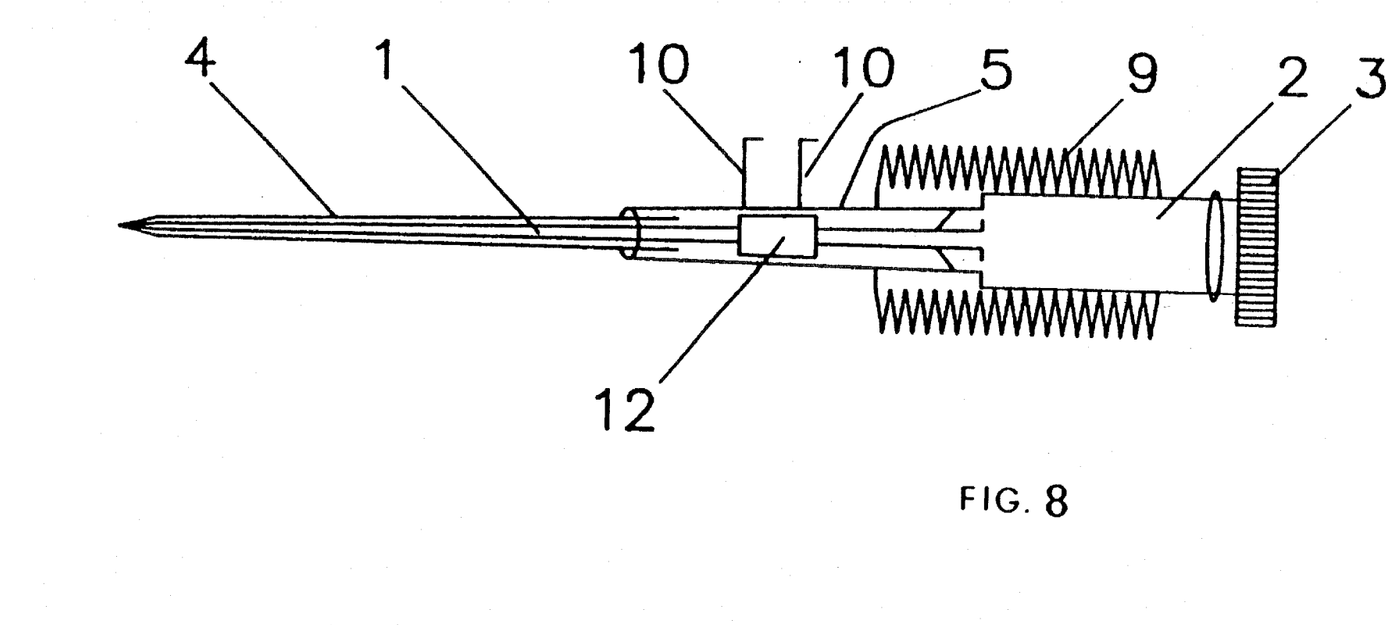
FIGS. 8 and 9 show yet again similar views to FIGS. 1 and 2 and illustrate a fourth form of construction for the invention.
Figure 9:
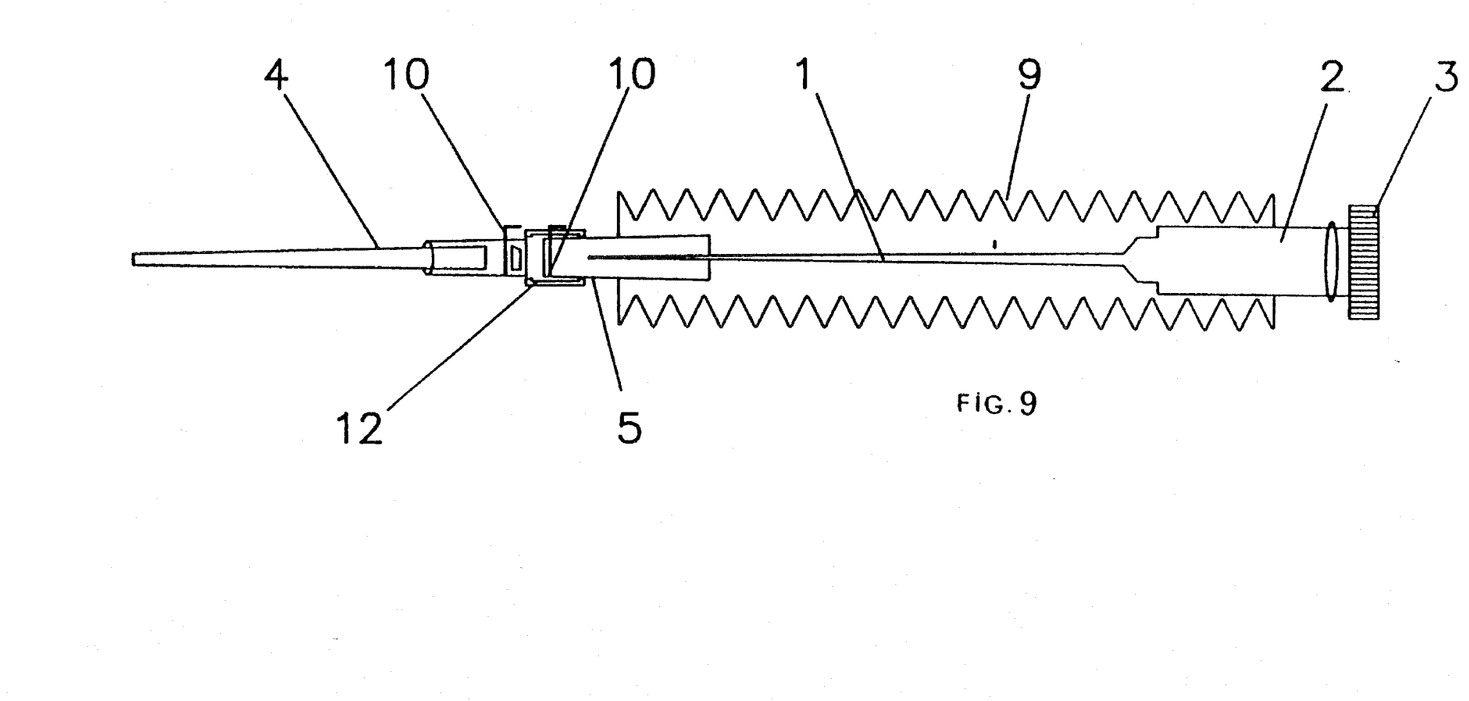
Figure 10:
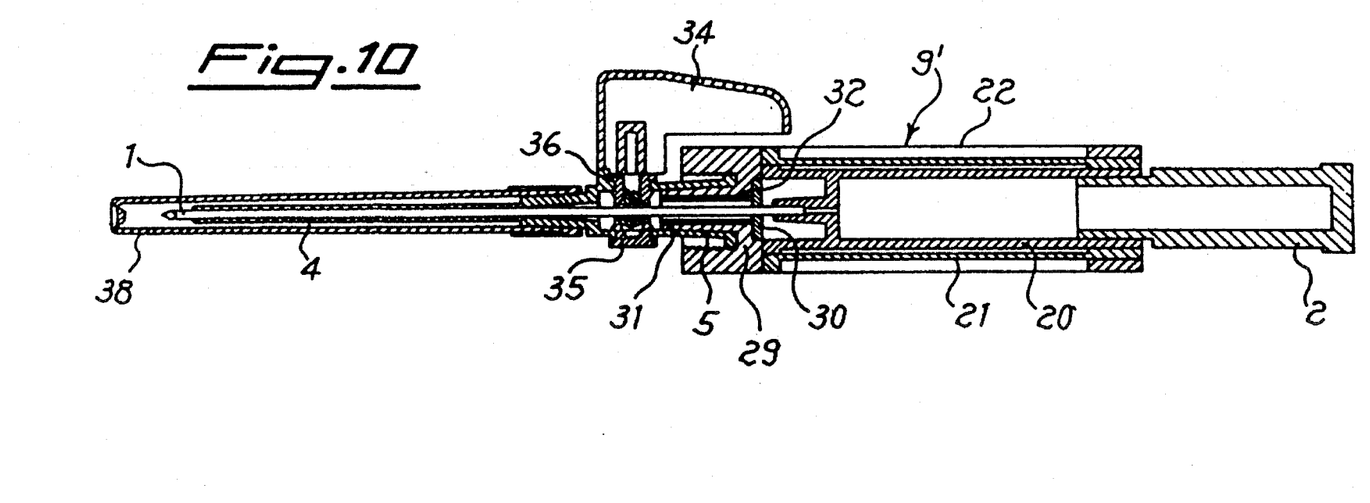
FIG. 10 represents a lateral view in section of a fifth and preferred form of construction of the needle catheter according to the invention and before the withdrawal of the metallic needle-guide.
Figure 11:
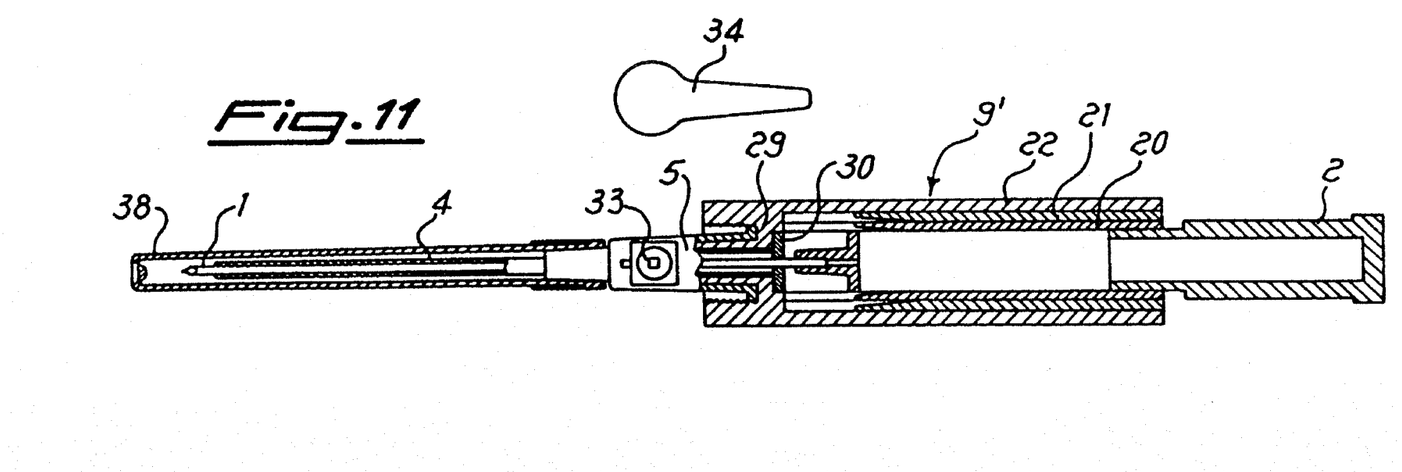
FIG. 11 represents a view, partly in section and which is at an angle of 90° with respect to that of FIG. 10.

The construction illustrated in FIGS. 8 and 9 corresponds substantially to that of FIGS. 6 and 7, with the sole difference that in this case, a simpler needle catheter is shown which does not have the flexible lateral connection (6).

For the administration of a drip or for other uses, a small auxiliary tube can be provided with one end screwed or grooved so as to be able to connect with the end of the part of the casing (5) which remains attached to the catheter (4).

The construction illustrated in FIGS. 10 to 14 differs from those described above principally by the fact that the extensible element, indicated globally by reference number (9'), is of the telescopic type and comprises three tubular elements (20), (21), (22) which is inserted one inside the other. The most internal element (20) is attached to the grip (2) of the needle (1) whereas the most external element (22) can be fixed to the casing (5) of the catheter (4).

The maximum telescopic extension of the group (9') is determined by the stop pegs (23), (24), protruding externally from the elements (20), (21) which engage respectively with pegs (25), (26) protruding internally from the elements (21), (22).

The blocking of the telescopic group in the condition of maximum extension is assured by elastic stop tongues (27), (28) set in the walls of the elements (20), (21) which bear on the posterior edges of the tubular elements (21), (22) respectively.

The most external tubular element (22) can be fixed to the casing (5) of the catheter by a screw thread as is shown on the attached sketch or by other suitable means, for example by a groove. A small holed plate is placed near the front end of element (22) holding internally a rubber stop (30) and extending externally (from the catheter (4)) with a spigot (31) which is inserted into the casing (5) of the catheter (4).

The rubber stop (30) made of natural rubber, polystyrol or similar) is penetrated by the needle (1) before use (FIGS. 10 and 11) and closes up again when the needle is retracted (FIGS. 12 and 13) to prevent blood from running out.

At least one internal part (32) of the spigot (31) is in spongy material to absorb the few drops of blood which might remain on the outside of the rubber stop (30) when the needle (1) is withdrawn.

A tap consisting of a ball valve (33) and operated by an external lever (34) is provided in the casing (5) of the catheter (4). The ball valve (33) is placed between two opposing ferrules (35), (36) and has an internal lumen (37) for the passage of the needle and of any liquid which may be administered to the patient.

Figure 12:
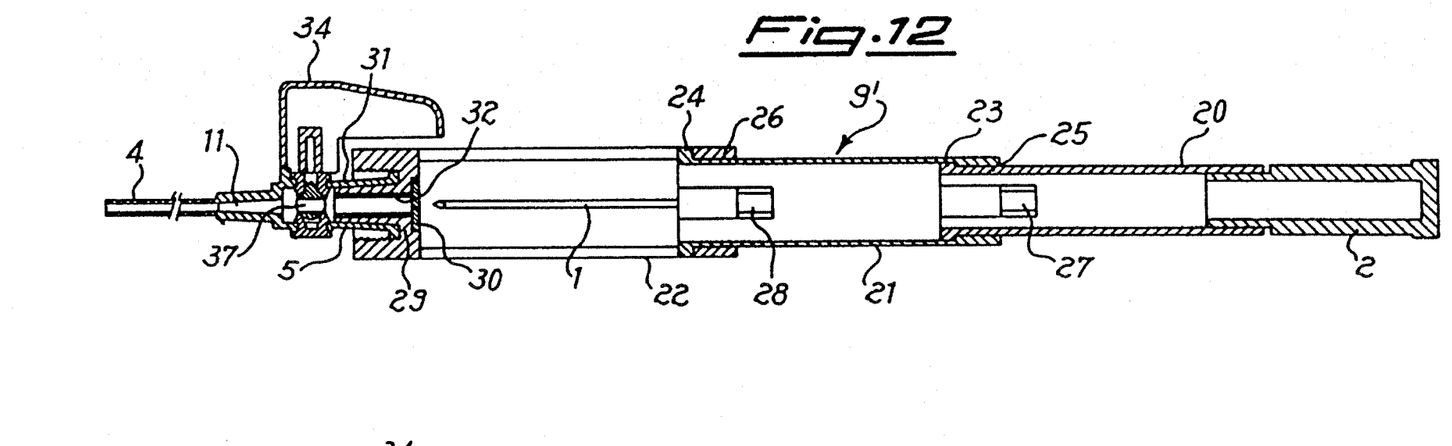
FIGS. 12 and 13 represent similar views to FIGS. 10 and 11 respectively but with the needle-guide retracted.
Figure 13:
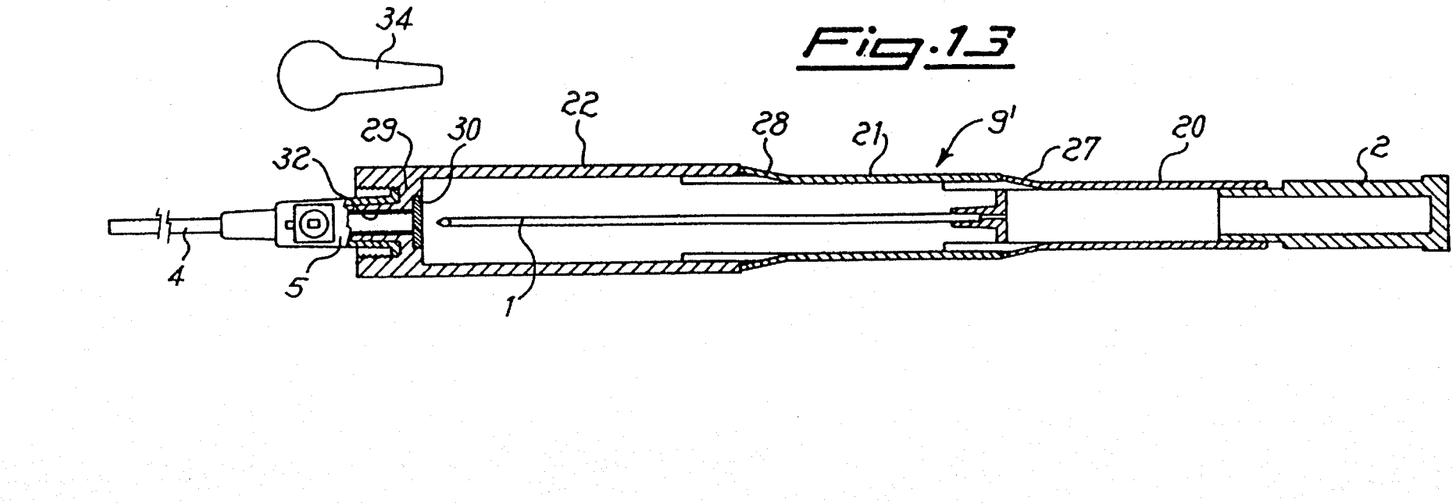
Figure 14:
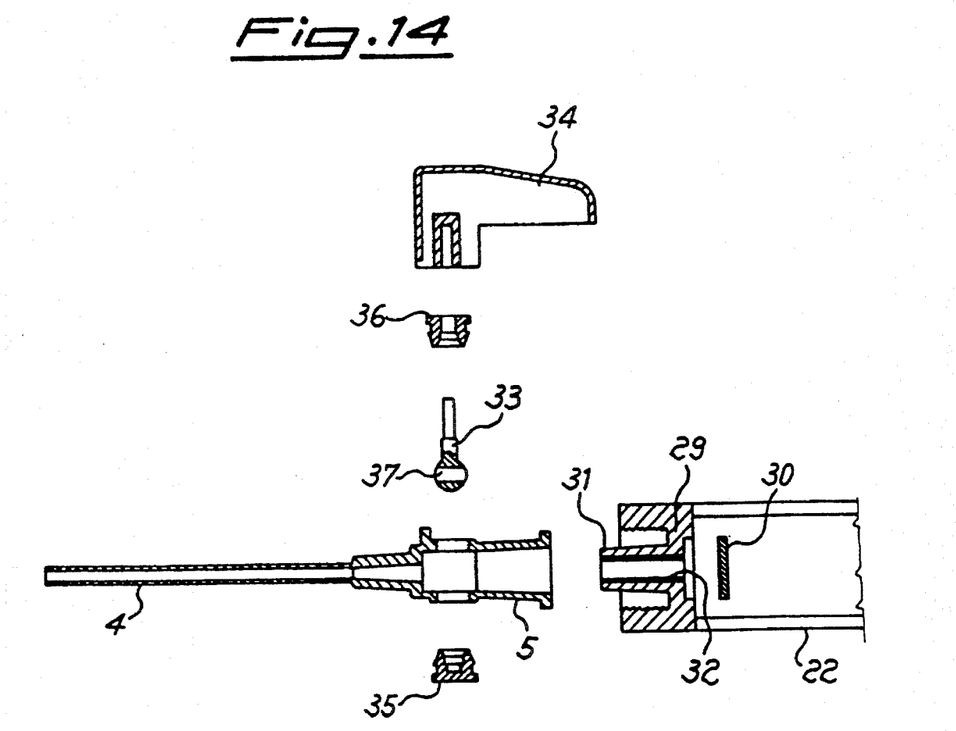
FIG. 14 represents an exploded view of the part of the needle catheter illustrated in FIG. 12.

When the needle is retracted by turning the lever (34) through 90°, the ball (33) occludes the lumen (11) of the casing (5) of the catheter and any outflow of blood is cut off.

Instead of the ball valve tap, another flow deviation means may be used, such as a tap placed inside the casing (5) of the catheter so as to be coaxial with the catheter itself, allowing the flow of liquids or of the metal needle-mandrel in one position and closing the passage when rotated of 90°.

In using the needle catheter according to this construction, when the needle has been retracted as shown in FIGS. 12 and 13, the ball valve (33) is closed by rotating the lever (34) through 90° and the telescopic group (9') containing the needle (1) is removed. When this is done, a tube for the administration of a drip or similar is connected to the top of the casing (5) of the catheter (4), and the valve (33) is re-opened by rotating the lever (34).

Naturally, even in this case a flexible lateral connection (6) can be made, joined to the casing (5) of the catheter (4) above the ball valve (33). In this case it is possible to leave the telescopic group (9') in situ during use.

It is evident that some of the methods introduced in the construction according to FIGS. 10 to 14, such as, for example, the flow interception valve (33), could also be used in the previously illustrated constructions in substitution of items with the same function and vice versa.

FIGS. 10 to 13 also show a cap (38) for the protection of the catheter (4) before use.

From what has been written above, it is clear the invention fulfils the defined objective in eliminating any risk whatever that the metallic needle guide could prick the user of the needle catheter according to the invention or prick the waste disposal workers. It likewise blocks the flow of blood after the extraction of the metallic needle.

We claim:

1. A needle catheter, which comprises a metallic needle-guide (1) consisting of a cannula having an end grip (2), a catheter (4), said catheter having an end casing (5) and covering said needle-guide (1), said casing having a lumen, an extensible element (9') positioned between said grip (2) of the needle-guide (1) and said casing (5) of said catheter (4), whereby said needle-guide (1) is covered when it is retracted, said extensible element (9') consisting of a telescopic group including inner, middle and outer tubular elements (20), (21), (22), said tubular element (20) being the innermost one and being fixed to said end grip (2) of said needle, the tubular element (22) being the outermost one and being fixed to said casing (5) of said catheter, a blocking system (27,28) for said needle when said needle is in the retracted position, said inner, middle and outer tubular elements (20,21,22) having walls, said blocking system being integral with said walls, means (33) for occluding the lumen of said casing, wherein said blocking system consists of elastic stop tongues, said middle and outer tubular elements (21) and (22) being adjacent and said inner and middle tubular elements (20) and (21) being adjacent, said inner and middle tubular elements (20) and (21) having rear edges, said elastic stop tongues bearing on said rear edges, said needle catheter further comprises stop means (23,24; 25,26) for limiting the maximum extension of said tubular elements, said needle catheter further comprises a rubber seal (30) closure attached to said casing (5) of said catheter (4), at least a part (32) of said rubber seal being made of spongy material, said needle-guide (1) penetrating said spongy material prior to the stage when the needle-guide is retracted, wherein said telescopic group (9') is movably fixed to said casing (5) of said catheter (4), and wherein said means for occluding the flow in the lumen (11) of said casing (5) of said catheter (4) consists of a tap (33), and the needle catheter comprises a lever (34), said lever being adapted to rotate, whereby rotation of said lever by 90° causes said tap to occlude the lumen of the casing.

2. The needle catheter according to claim 1 wherein said tap is a ball contained in said casing (5) of said catheter (4), said ball being movable into the lumen (11) of said casing (5) by application of pressure.

3. A needle catheter, which comprises a metallic needle-guide (1) consisting of a cannula having an end grip (2), a catheter (4), said catheter having an end casing (5) and covering said needle-guide (1), said casing having a lumen, an extensible element (9') positioned between said grip (2) of the needle-guide (1) and said casing (5) of said catheter (4), whereby said needle-guide (1) is covered when it is retracted, said extensible element (9') consisting of a telescopic group including inner, middle and outer tubular elements (20), (21), (22), said tubular element (20) being the innermost one and being fixed to said end grip (2) of said needle, the tubular element (22) being the outermost one and being fixed to said casing (5) of said catheter, a blocking system (27,28) for said needle when said needle is in the retracted position, said inner, middle and outer tubular elements (20,21,22) having walls, said blocking system being integral with said walls, means (33) for occluding the lumen of said casing, wherein said blocking system consists of elastic stop tongues, said middle and outer tubular elements (21) and (22) being adjacent and said inner and middle tubular elements (20) and (21) being adjacent, said inner and middle tubular elements (20) and (21) having rear edges, said elastic stop tongues bearing on said rear edges, said needle catheter further comprises stop means (23,24; 25,26) for limiting the maximum extension of said tubular elements, said needle catheter further comprises a rubber seal (30) closure attached to said casing (5) of said catheter (4), at least a part (32) of said rubber seal being made of spongy material, said needle-guide (1) penetrating said spongy material prior to the stage when the needle-guide is retracted, wherein said telescopic group (9') is movably fixed to said casing (5) of said catheter (4), and wherein said means for occluding the flow in the lumen of the casing consists of an adjustable vane movable from a raised position in which it does not obstruct the lumen (11) of the casing (5) of the catheter, to a lowered position in which it occludes the lumen.

4. The needle catheter according to claim 3 wherein two vanes are provided in said casing (5) of said catheter (4), whereby said casing is divided into two parts and said needle catheter comprises means (12) for holding said parts together.

5. The needle catheter according to claim 4 which comprises a flexible lateral connection (6), said lateral connection being positioned above said blocking system, said blocking system being located in the casing (5).

* * * * *